(12) United States Patent
Vincent

(10) Patent No.: US 8,001,829 B2
(45) Date of Patent: Aug. 23, 2011

(54) APPARATUS FOR SENSING AT LEAST ONE PARAMETER IN A LIQUID

(75) Inventor: David Robert Vincent, West Moors (GB)

(73) Assignee: Intellitect Water Limited, Dorset (GB)

( * ) Notice: Subject to any disclaimer, the term of this patent is extended or adjusted under 35 U.S.C. 154(b) by 596 days.

(21) Appl. No.: 12/087,842

(22) PCT Filed: Jan. 16, 2007

(86) PCT No.: PCT/GB2007/000110
§ 371 (c)(1),
(2), (4) Date: Jul. 16, 2008

(87) PCT Pub. No.: WO2007/083095
PCT Pub. Date: Jul. 26, 2007

(65) Prior Publication Data
US 2009/0000356 A1    Jan. 1, 2009

(30) Foreign Application Priority Data
Jan. 20, 2006  (GB) .................................. 0601185.2

(51) Int. Cl.
*G01N 11/14* (2006.01)

(52) U.S. Cl. ........................................................ 73/54.35
(58) Field of Classification Search ................. 73/54.23, 73/54.28, 54.29, 54.31–51.35
See application file for complete search history.

(56) References Cited

U.S. PATENT DOCUMENTS

| | | | |
|---|---|---|---|
| 4,144,745 A * | 3/1979 | Sivill | 73/54.31 |
| 4,352,287 A * | 10/1982 | Orth et al. | 73/54.39 |
| 4,763,537 A | 8/1988 | Scott et al. | |
| 6,499,336 B1 * | 12/2002 | Raffer | 73/54.28 |
| 2001/0011642 A1 | 8/2001 | Fukunaga et al. | |
| 2005/0178703 A1 | 8/2005 | Newman | |

FOREIGN PATENT DOCUMENTS

JP    11 053661 A    2/1999

\* cited by examiner

*Primary Examiner* — John Fitzgerald
(74) *Attorney, Agent, or Firm* — Iandiorio Teska & Coleman

(57) ABSTRACT

An apparatus for sensing at least one parameter in a liquid including a sensor means for sensing the parameter, a rotation means and a drive generator means for driving the rotation means as well as to generate electricity passed to an electricity storage means. In addition to a control means for operating the rotation means which also operates in a flow of the liquid and in which the rotation means maintains the flow of liquid at or above a predetermined value.

15 Claims, 3 Drawing Sheets

APPARATUS FOR SENSING AT LEAST ONE PARAMETER IN A LIQUID

BACKGROUND OF THE INVENTION

This invention relates to apparatus for sensing at least one parameter in a liquid. The liquid may be water and the parameters that may be sensed are, for example, chlorine content in water, and oxygen content in water. The apparatus may be especially useful for measuring water quality in potable water distribution networks.

It is known to deploy large numbers of remote sensors in potable water distribution networks, in order to measure various parameters in the water. The distribution of the sensors in a potable water distribution network may encounter two problems. The first problem is that an adequate flow of water is required to the sensors. This is because some electrochemical measurements that may be undertaken require flow. Also, an adequate flow is required to reduce fouling in the networks due to an inadequate flow rate. The second problem is that of electrical power consumption consumed by the remote sensors during operation. Probes incorporating built-in rotation means for increasing water flow consume too much power. It is often not possible to recharge batteries sufficiently frequently and/or it is often not possible to install mains power or other power generators, for example solar power generators, due to the sensor sites being too remote and/or inaccessible.

It is an aim of the present invention to obviate or reduce the above mentioned problems.

BRIEF SUMMARY OF THE INVENTION

Accordingly in one non-limiting embodiment of the present invention there is provided apparatus for sensing at least one parameter in a liquid, which apparatus comprises sensor means for sensing the parameter in the liquid, rotation means, drive and generator means for driving the rotation means and generating electricity, electricity storage means, and control means, the apparatus being such that in use the rotation means operates in a flow of the liquid, the drive and generator means drives the rotation means when the flow of liquid is below a predetermined value whereby the rotation means maintains the flow of liquid at or above the predetermined value, the drive and generator means is driven by electricity from the electricity storage means, the flow of liquid drives the rotation means when the flow of liquid is at or above the predetermined value, the drive and generator means is operated by the rotation means when the rotation means is driven by the flow of liquid, electricity generated by the drive and generator means is stored in the electricity storage means for use in driving the drive and generator means, and the control means controls the operation of the apparatus consequent upon the rate of flow of the liquid.

The apparatus of the present invention is thus able to eliminate low liquid flow problems by use of the rotation means as and when required. The apparatus of the present invention is able to reduce battery life problems by in-situ power generation by the electricity generating means. Preferably, the apparatus of the present invention is for use in potable water distribution networks, in which case the liquid will be water. The apparatus of the present invention may however be used with other liquids if desired. When used in water distribution networks, the apparatus will usually be installed in appropriate pipes or other conduits containing the water.

The apparatus may be one in which the drive and generator means is formed by a single motor-generator device.

The apparatus may be one in which the motor-generator device has a motor drive circuit and an electricity generating circuit, and in which the control means has a control circuit which is operatively connected to the motor drive circuit and the electricity generating circuit. The apparatus may be one in which the motor-generator device comprises electricity generating means formed as an integral part of an electric motor. In this case, the electricity generating circuit may be connected to coils in the electric motor, whereby rotation of the rotation means by the flow of water causes generation of an electromotive force which generates the electricity. The generated electricity can be rectified by rectifier means and then used to charge the electricity storage means.

In an alternative embodiment of the invention, the apparatus may be one in which the drive and generator means is formed by an electric motor which drives the rotation means, and a separate electricity generating means for generating electricity.

Preferably, the drive and generator means is connected to the rotation means by a magnetic coupling. The use of a magnetic coupling enables the drive and generator means to be completely encased in a housing, for example a stainless steel housing. Thus the drive and generator means is not affected by the operation of the rotation means, even if the rotation means is operating in water at a high pressure. Other means of connecting the drive and generator means to the rotation means may be employed so that, for example, the drive and generator means may be connected to the rotation means by a mechanical seal. The mechanical seal will be chosen to allow long automatic use of the apparatus of the invention without the mechanical seal developing a leak.

In all embodiments of the invention, the electric motor may be a brushless direct current motor.

The rotation means may be of a propeller shape. The rotation means may be of any suitable and appropriate shape for increasing the flow of liquid as and when required. Preferably, the rotation means is of a shape which facilitates rotation of the rotation means by a flow of the liquid parallel to a plane of the rotation means. In this case, the rotation means may be a disc having a plurality of vanes mounted on the disc.

The vanes may be mounted on the disc such that the vanes are pushed down when they are travelling against the direction of flow of the liquid, and they are pushed up when they are travelling with the direction of flow of the liquid. In order to enable this movement of the vanes, the vanes may be mounted by hinges on the disc. Other means of mounting the vanes on the disc may be employed.

Usually, the vanes will be mounted on one side of the disc. If desired however the vanes may be mounted on both sides of the disc.

The electricity storage means will usually be a battery. Other types of electricity storage means may however be employed so that, for example, the electricity storage means may be a super capacitor.

Any suitable and appropriate type of sensor means for sensing one or more desired parameters in the liquid may be employed. Thus, for example, the sensor means may sense chlorine content in the water and/or oxygen content in the water.

The present invention also extends to a combination of a liquid distribution network, a liquid in the network, and a plurality of units of apparatus of the invention in the network.

The control means may operated indirectly by monitoring the rate of flow of the liquid (for example the flow of liquid running in a pipe without operation of the rotation means) using a separate flow sensor (away from the rotation means) and switching the mode accordingly via a microprocessor or other computing device. Alternatively, the control means may operate by using the electrical power generated or the electrical power required to operate the rotation means as a measure of the ambient flow. This method may use the shape of the rotation means, with the rotation means being such that it is pushed more favourably in one direction than the other. In order to achieve this, the rotation means may have vanes as mentioned above. The vanes may be flexibly attached to a central axis. The vanes may have a profile that further enhances the directionality of the device. The profile may be curved profile or a V-shape profile. By stirring against the direction favoured by electrical power generation, as the flow increases, the electrical power required will increase. This electrical power may be compared against a reference value, and the operating mode switched (hysteretically) to generating mode. Conversely, if the rotation means is turned in the direction favoured by electrical power generation, current required will drop as the fluid flow increases. With such a mode, power will be saved. If the motor drive circuit is switched off, and the electrical power generation circuit is switched on, electrical power may thus be stored for future use.

In order to minimise wear, magnetic bearings may be employed.

The apparatus of the present invention may be especially useful in underground situations in pipes, where other methods of generating electricity for the electricity storage means are unsuitable. As indicated above, the liquid will usually be potable water in a water distribution network. Other types of liquids may however be employed including, for example non-potable water. The liquid may also be installed in various other types of flowing environments. Depending upon conditions of installation, the apparatus may be able to operate automatically for long periods of time without external power requirements.

BRIEF DESCRIPTION OF THE DRAWINGS

Embodiments of the invention will now be described solely by way of example and with reference to the accompanying drawings in which.

DETAILED DESCRIPTION OF THE INVENTION

Figure 1:
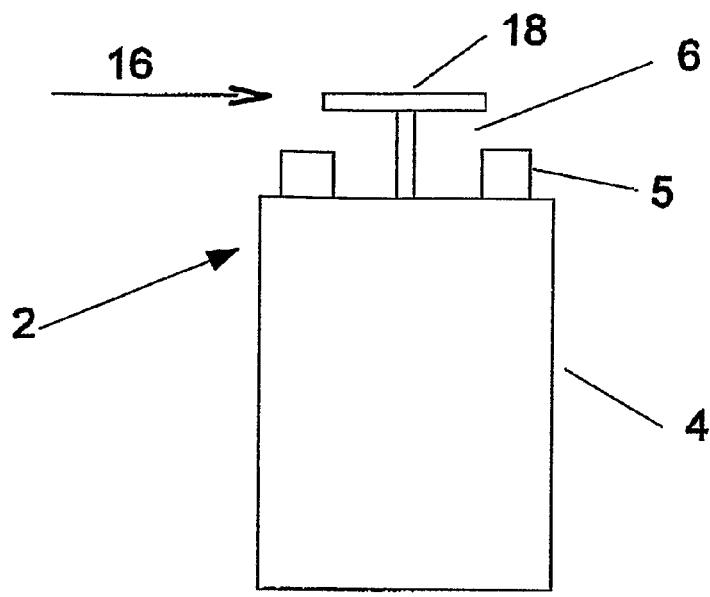
FIG. 1 shows apparatus of the present invention.
Figure 2:
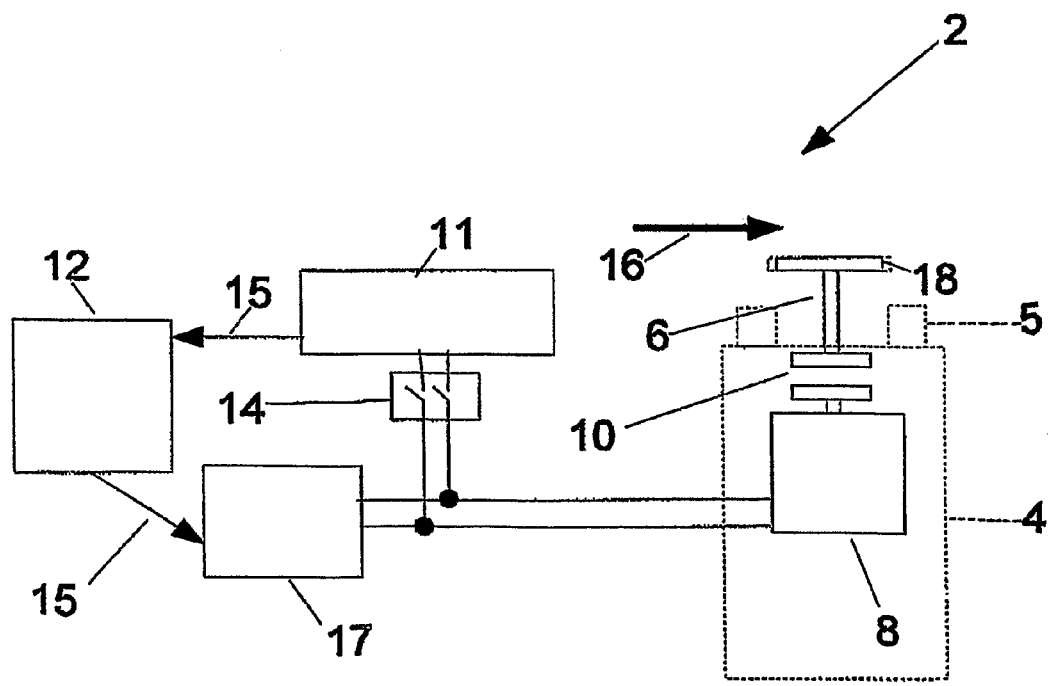
FIG. 2 is a schematic view of the electrical and mechanical components of the apparatus of the present invention.

Referring to FIGS. 1 and 2, there is shown apparatus 2 for sensing at least one parameter in a liquid. The apparatus 2 comprises sensor means 4. The sensor means 4 may be a sonde having a number of different flow-sensitive sensors 5. The apparatus 2 also comprises rotation means 6, and drive and generator means 8. In one mode of operation, the drive and generator means 8 drives the rotation means 6 via a magnetic coupling 10. In an alternative mode of operation, the drive and generator means 8 operates to generate electrical power. The apparatus 2 further comprises electricity storage means 12. Control means 14 controls operation of the apparatus 2.

The apparatus 2 is such that in use, the rotation means 6 operates in the liquid 16. As can be seen from FIG. 1, the liquid 16 is such that it directly engages the sensor means 4 and the rotation means 6. The rotation means 6 comprises a disc 18 and a plurality of vanes (not shown in FIGS. 1 and 2). Rotation of the rotation means 6 is counter-clockwise.

The apparatus 2 is such that the drive and generator means 8 drives the rotation means 6 when the flow of liquid 16 is below a predetermined value. Thus the rotation means 6 maintains the flow of liquid at or above the predetermined value. The drive and generator means 8 is driven by electricity from the electricity storage means 12.

The apparatus 2 is such that the flow of liquid 16 drives the rotation means 6 when the flow of liquid 16 is at or above the predetermined value. The drive and generator means 8, operating as an electricity generating means, is operated by the rotation means 6 when the rotation means 6 is driven by the flow of liquid 16. Electricity generated by the drive and generator means 8, operating as the electricity generating means, is converted and regulated by electric power conversion means in the form of an electricity generating circuit 11. The generated electricity is stored in the electric storage means 12 for use in driving the drive and generator means 8. The direction of electrical power and flow are shown by arrows 15.

The control means 14 controls the operation of the apparatus 2 consequent upon the rate of flow of the liquid 16. The drive and generator means 8 has a motor drive circuit 17 and the electricity generating circuit 11. The control means 14 has a control circuit which is operatively connected to the motor drive circuit and the electricity generating circuit. The electricity generating circuit is connected to coils (not shown) in the electric motor part of the drive and generator means 8. Thus rotation of the rotation means 6 by the flow of water causes generation of an electromotive force which generates the electricity. The electricity generating circuit 11 includes a rectifier which rectifies the generated current so that it is then suitable for storage in the electricity storage means 12, which will usually be a battery.

The drive and generator means 8 is connected to the rotation means 6 by a magnetic coupling 10. The drive and generator means 8 is then able to be housed in a stainless steel housing which is sealed against the ingress of liquid.

Referring now to FIGS. 3-6, there is shown an example of rotation means 24. The rotation means 24 is shown receiving liquid 16. The rotation means 24 is of a shape which facilitates rotation of the rotation means 24 by a flow of the liquid 16 which is parallel to a plane of the rotation means 24. The rotation means 24 is a disc 28 having a plurality of vanes 30, 38 mounted on one side of the disc 28. Rotation of the rotation means 24 is counter-clockwise as shown by arrow 32. Rotation of the rotation means 18 is about a central axis 34.

Figure 3:
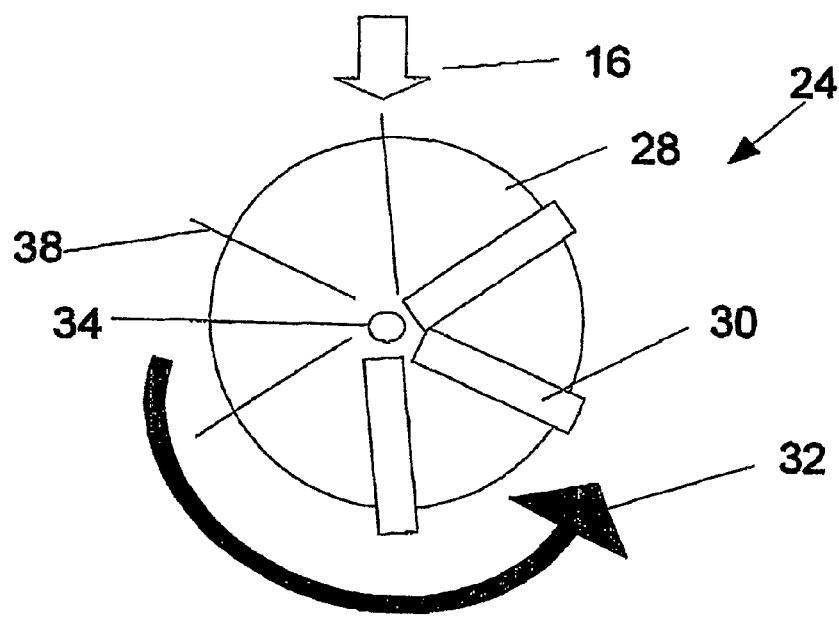
FIG. 3 is a top plan view of preferred rotation means forming part of the apparatus of the present invention.
Figure 4:
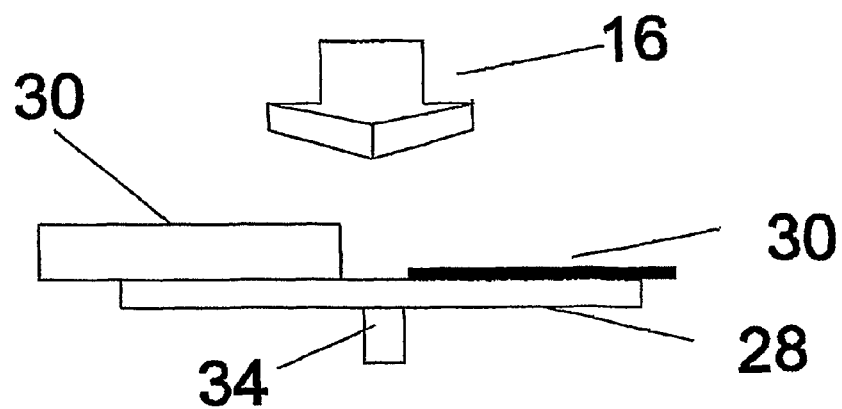
FIGS. 4, 5 and 6 illustrate operation of the rotation means shown in FIG. 3.
Figure 5:
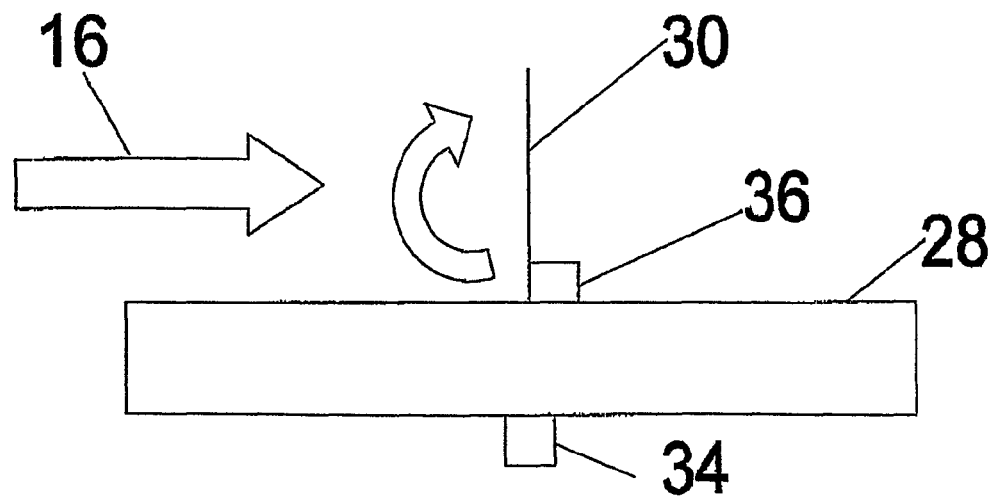
Figure 6:
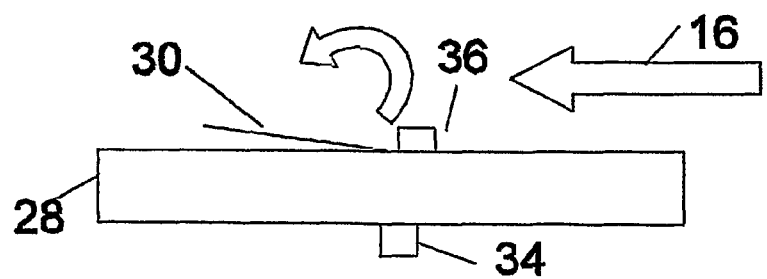

As can best be appreciated from FIGS. 4, 5 and 6, the rotation means 24 is such that the vanes 30 are mounted on the disc 28 by hinges 36 such that the vanes 30 are pushed down when the vanes 30 are travelling against the flow of liquid 26, and the vanes 30 are pushed up when the vanes 30 are travelling with the direction of flow of the liquid 26. In FIG. 3, the direction of flow relative to the vanes causing the vanes 30 to be pushed up is shown by the liquid 16.

It is to be appreciated that the embodiments of the invention described above with reference to the accompanying drawings have been given by way of example only and that modifications may be effected. Thus, for example, other types of rotation means 6 and drive and generator means 8 may be employed. The drive and generator means for the present invention may be a motor-generator which is a single power transducer that can be used as either an electric motor or a generator, converting between electrical power and mechanical power. In principle, an electrical generator can also serve as an electric motor, or vice versa. A device that is specifically designed for use in either mode may be called a motor-generator.

The invention claimed is:

1. Apparatus for sensing at least one parameter in a liquid, which apparatus comprises sensor means for sensing the parameter in the liquid, rotation means, drive and generator means for driving the rotation means and generating electricity, electricity storage means, and control means, the apparatus being such that in use the rotation means operates in a flow of the liquid, the drive and generator means drives the rotation means when the flow of liquid is below a predetermined value whereby the rotation means maintains the flow of liquid at or above the predetermined value, the drive and generator means is driven by electricity from the electricity storage means, the flow of liquid drives the rotation means when the flow of liquid is at or above the predetermined value, the drive and generator means is operated by the rotation means when the rotation means is driven by the flow of liquid, electricity generated by the drive and generator means is stored in the electricity storage means for use in driving the drive and generator means, and the control means controls the operation of the apparatus consequent upon the rate of flow of the liquid.

2. Apparatus according to claim 1 in which the drive and generator means is formed by an electronic motor which drives the rotation means, and a separate electricity generating means for generating electricity.

3. Apparatus according to claim 1 in which the drive and generator means is connected to the rotation means by a magnetic coupling.

4. Apparatus according to claim 1 in which the drive and generator means is connected to the rotation means by a mechanical seal.

5. Apparatus according to claim 1 in which the electricity storage means is a battery or a supercapcitor.

6. The combination of a liquid distribution network, a liquid in the network, and a plurality of units of the apparatus according to claim 1.

7. Apparatus according to claim 1 in which the drive and generator means is formed by single motor-generator device.

8. Apparatus according to claim 7 in which the motor-generator device has a motor drive circuit and an electricity generating circuit, and in which the control means has a control circuit which is operatively connected to the motor drive circuit and the electricity generating circuit.

9. Apparatus according to claim 8 in which the motor-generator device comprises electricity generating means formed as an integral part of the electric motor.

10. Apparatus according to claim 8 in which the electricity generating circuit is connected to coils in the electric motor, whereby rotation of the rotation means by the flow of water causes generation of an electromotive force which generates the electricity.

11. Apparatus according to claim 1 in which the rotation means is of a shape which facilitates rotation of the rotation means by a flow of the liquid parallel to a plane of the rotation means.

12. Apparatus according to claim 11 in which the rotation means is a disc having a plurality of vanes mounted on the disc.

13. Apparatus according to claim 12 in which the vanes are mounted on one side of the disc.

14. Apparatus according to claim 12 in which the vanes are mounted on the disc such that the vanes are pushed down when they are traveling against the direction of flow of the liquid, and they are pushed up when they are traveling with the direction of flow of the liquid.

15. Apparatus according to claim 14 which the vanes are mounted by hinges on the disc.

* * * * *